(12) United States Patent
Sato

(10) Patent No.: US 8,941,059 B2
(45) Date of Patent: Jan. 27, 2015

(54) SAMPLING APPARATUS

(75) Inventor: Tomoyoshi Sato, Ibaraki (JP)

(73) Assignee: Atonarp, Inc., Hachioji-Shi, Tokyo (JP)

( * ) Notice: Subject to any disclaimer, the term of this patent is extended or adjusted under 35 U.S.C. 154(b) by 0 days.

(21) Appl. No.: 13/702,097

(22) PCT Filed: Oct. 31, 2011

(86) PCT No.: PCT/JP2011/006100
§ 371 (c)(1),
(2), (4) Date: Feb. 12, 2013

(87) PCT Pub. No.: WO2012/056729
PCT Pub. Date: May 3, 2012

(65) Prior Publication Data
US 2013/0211211 A1 Aug. 15, 2013

(30) Foreign Application Priority Data
Oct. 29, 2010 (JP) .................. 2010-243961

(51) Int. Cl.
| H01J 49/26 | (2006.01) |
| H01J 49/04 | (2006.01) |
| A61B 10/00 | (2006.01) |
| A61B 5/00 | (2006.01) |
| A61B 10/02 | (2006.01) |
| G01N 33/497 | (2006.01) |

(Continued)

(52) U.S. Cl.
CPC ............ *H01J 49/04* (2013.01); *A61B 10/0045* (2013.01); *A61B 5/4869* (2013.01); *A61B 10/02* (2013.01); *A61B 10/0051* (2013.01); *A61B 10/0064* (2013.01); *G01N 33/497* (2013.01); *G01N 2800/20* (2013.01); *G01N 2001/028* (2013.01); *G01N 27/624* (2013.01)
USPC ............................ 250/288; 250/281; 250/282

(58) Field of Classification Search
USPC ........................... 250/281, 282, 288
See application file for complete search history.

(56) References Cited

U.S. PATENT DOCUMENTS

| 2008/0054174 A1* | 3/2008 | Boyle et al. ............ 250/286 |
| 2011/0198501 A1* | 8/2011 | Ouchi et al. ............ 250/343 |

FOREIGN PATENT DOCUMENTS

| JP | 11-506624 | 6/1999 |
| JP | 2006-138731 | 6/2006 |
| JP | 2006-214747 A | 8/2006 |

(Continued)

OTHER PUBLICATIONS

International Search Report from corresponding international application No. PCT/JP2011/006100, mailing date Dec. 27, 2011 (English translation provided).

(Continued)

*Primary Examiner* — Nicole Ippolito
(74) *Attorney, Agent, or Firm* — Buchanan Ingersoll & Rooney PC

(57) ABSTRACT

There is provided a chip-type sampling apparatus to be attached so that a sampling side of the sampling apparatus faces the skin, the apparatus including a porous adsorption layer that faces the sampling side and has a pore diameter in a range of 0.1 to 1000 nm. One example of the adsorption layer includes at least three porous layers with different central pore diameters that are laminated from the sampling side in descending order of the central pore diameters. The sampling apparatus should preferably also include a layer that sucks air through the adsorption layer.

6 Claims, 6 Drawing Sheets

(51) Int. Cl.
  *G01N 1/02* (2006.01)
  *G01N 27/62* (2006.01)

(56) References Cited

FOREIGN PATENT DOCUMENTS

| JP | 2006-334511 A | 12/2006 |
| JP | 2010-169658 A | 8/2010 |
| WO | WO-2006/013396 | 2/2006 |

OTHER PUBLICATIONS

International Preliminary Report on Patentability issued in corresponding PCT Application No. PCT/JP2011/006100 mailed May 14, 2013.

Takao Tsuda, "Hito Hifu Kara Kisan sareru Kagaku Busshitsu to Kaori", Aroma Research, No. 33; vol. 9, No. 1, Feb. 28, 2008, pp. 63-72, with English abstract.

* cited by examiner

US 8,941,059 B2

SAMPLING APPARATUS

TECHNICAL FIELD

The present invention relates to an apparatus that samples chemical substances or the like.

BACKGROUND ART

In recent years, attention has been focused on apparatuses called field asymmetric waveform ion mobility spectrometers (FAIMS) as a technology for detecting and analyzing chemical substances with high sensitivity. In such an apparatus, by changing the DC voltage and the AC voltage applied to sensors, it is possible to detect changes in the mobility of ionized chemical substances using a fine filter and to specify chemical substances according to differences in such detection results.

WO2006/013396 (Japanese Patent Application No. 2008-508693) discloses an ion mobility spectrometer with an ion filter in the form of at least one ion channel that includes a plurality of electrodes. With this ion mobility spectrometer, a time-varying electric potential applied to the conductive layers allows the filter to selectively admit ion species. Such potential has a drive electric field component and a transverse electric field component, and in a preferred embodiment, the respective electrodes contribute to the generation of both the drive electric field component and the transverse electric field component. Such device can be used even without a drift gas flow. In addition, such publication discloses a micromachining technology for manufacturing a microscale spectrometer for the various applications of a spectrometer.

DISCLOSURE OF THE INVENTION

It is known that the constituents of a smell emitted from the body of a human or an animal, such as constituents included in skin respiration, change due to cancer or other diseases. To determine an initial state of cancer or other diseases or the progress of a disease, it is effective to analyze chemical substances of biological origin that are emitted from the body.

One aspect of the present invention is a chip-type sampling apparatus to be attached so that a sampling side of the sampling apparatus faces the skin. Such sampling apparatus includes a porous adsorption layer that faces the sampling side and has a pore diameter in a range of 0.1 to 1000 nm. Instead of directly measuring chemical substances emitted from an organism using an ion mobility sensor or the like, the sampling apparatus is attached to the organism and chemical substances emitted from the organism are temporarily adsorbed by the sampling apparatus. This means that after chemical substances of biological origin emitted from the skin have been collected, it is possible to analyze the chemical substances of biological origin using an ion mobility sensor or the like. Using a porous adsorption layer with a pore diameter suited to adsorption of molecules, bacteria, viruses or cells, it is possible to select and/or concentrate the analysis target (subject to analysis) at the sampling stage.

Another aspect of the present invention is a method, for example, a measuring method or a diagnosing method, including the following steps.

Attaching a sampling apparatus with the sampling side facing the skin and collecting a chemical substance emitted from an organism in the adsorption layer.

Heating the sampling apparatus that has been separated from the skin and analyzing a chemical substance of biological origin emitted from the sampling apparatus using an ion mobility sensor.

The adsorption layer should preferably include at least three porous layers with different central pore diameters (central fine pore diameters, average pore diameters), the at least three porous layers being laminated from the sampling side in descending order of average pore diameter. By sandwiching a porous layer with an average pore diameter suited to adsorption of the chemical substances to be analyzed, for example, molecules, between a porous layer with a larger average pore diameter and a porous layer with a smaller average pore diameter, it is easy to selectively concentrate the chemical substance to be analyzed.

In addition, it is preferable to provide a suction layer, via a flow control layer that controls passing airflow, on a non-sampling side of the adsorption layer. The suction layer sucks at least one of oxygen and nitrogen through the adsorption layer. Since it is possible with the suction layer to form a flow of air from the sampling side to the non-sampling side, it is possible to draw the chemical substance to be analyzed into the adsorption layer from the surface on the sampling side. This makes it easy to concentrate the chemical substance to be analyzed inside the adsorption layer.

A typical example of a suction layer is a layer placed under negative pressure. The suction layer may include a material, for example zeolite (a molecular sieve) of an appropriate pore diameter that adsorbs at least one of oxygen and nitrogen. The suction layer may include a material that reacts with at least one of oxygen and nitrogen, for example a material that forms oxide and/or nitride with comparatively high efficiency at room temperature or near body temperature.

A typical porous layer is a porous glass layer with little deviation in pore diameter manufactured according to a method such as sol gel.

DETAIL DESCRIPTION

Figure 1:
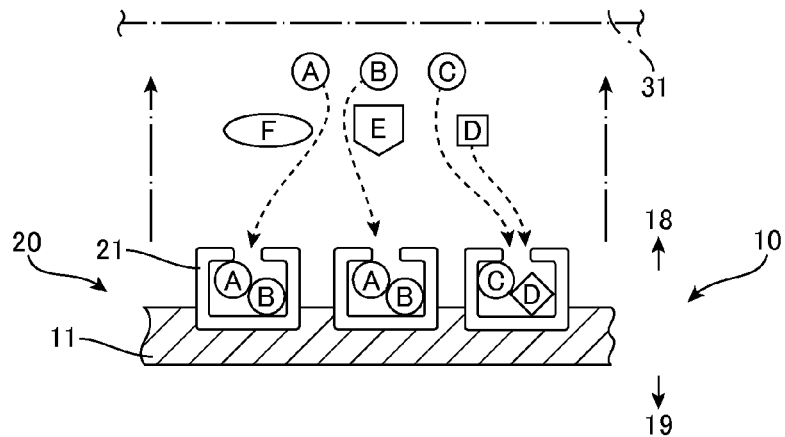
FIG. 1 is a diagram showing the overall construction of a sampler.

FIG. 1 shows an overview of a sampling apparatus (sampler). This sampler 10 includes a base 11 and a porous adsorption layer 20 that is fixed by an appropriate method to the surface (sampling-side) 18 of the base 11. One example of the porous adsorption layer 20 has porous glass beads 21 or zeolite, with an average pore diameter (central pore diameter, central fine pore diameter) of 0.1 nm to 10 nm, more preferably 0.3 nm to 5 nm, or even more preferably around 0.5 nm to 2 nm, held on the sampling side 18 of the base 11. This sampler 10 is attached by an appropriate method so that the sampling side 18 faces the skin 31 of a body. Typical methods of attaching the sampler 10 are fixing the sampler 10 to underwear or sticking the sampler 10 to the skin 31 using tape.

The cause of odors (smells, scents) emitted from the skin 31 due to skin respiration and the like are thought to be hydrocarbon compounds, and in particular aromatic compounds that include aromatic hydrocarbon compounds. The diameter (maximum size, maximum length) of many molecules of such aromatic compounds with a molecular weight of around 1 kDa or below is around 0.5 nm to 1.0 or up to around 2 nm. As one example, the diameter of a benzene ring is around 0.5 nm to 0.6 nm, and the pore diameter of the adsorption layer 20 should preferably be sized so that one or a number of aromatic compounds may enter.

As shown in FIG. 1, out of the substances A to F emitted from the skin 31, the sampler 10 is suited to adsorbing substances A to D, which for example are aromatic compounds with comparatively low molecular weights, such as xylene, toluene, ethylbenzene, and styrene. On the other hand, it is difficult to adsorb substances E and F, which for example are macromolecules such as peptides or small molecule proteins with a molecular weight of 5 kDa to several hundred (above 100) kDa and have a (maximum) molecular diameter of around 3 nm to 10 or up to around 20 nm. It is also hard for molecules of oxygen, nitrogen, and carbon dioxide with a diameter of 0.4 nm or below to be adsorbed, which makes it possible to selectively adsorb and concentrate odor (body odor) constituents.

As one of another examples, for a sampler 10 intended for macromolecules such as peptides or small molecule proteins with a molecular weight of several kDa to several hundred kDa and a molecular diameter of around 3 nm to 10 or up to around 20 nm, a sampler with an adsorption layer 20 including porous glass with a central diameter of around 10 to 20 nm is preferable. Yet one of another examples, for a sampler 10 intended for even larger macromolecules with a molecular weight of several thousand kDa and a molecular diameter of around 20 or so nm to 30 or up to around 40 nm, a sampler with an adsorption layer 20 including porous glass with a central diameter of around 25 to 30 or up to around 40 nm is preferable. Note that although the distribution of fine pores to the central diameter or average diameter is low for porous glass manufactured using zeolite (a molecular sieve), sol gel, or the like, in some cases there is a spread of around ±50%. Accordingly, it is preferable to also evaluate the distribution of fine pore diameters and determine the central diameter of the adsorbent substance relative to the diameter of the molecules (chemical substances) to be sampled.

Examples of the base 11 include non-woven fabric and a polymer sheet. By attaching an adsorbent material 21 such as zeolite or porous glass to the sampling side 18 of the base 11 using pressure or adhesive, it is possible to manufacture the sampler 10 with the adsorption layer 20 on the sampling side 18 of the base 11. By attaching such sampler 10 to the body surface so as to typically contact the skin 31 for a period from several minutes to several hours, it is possible to sample chemical substances (body odor constituents) of biological origin that are emitted from the human body or the body of an animal.

Figure 2:
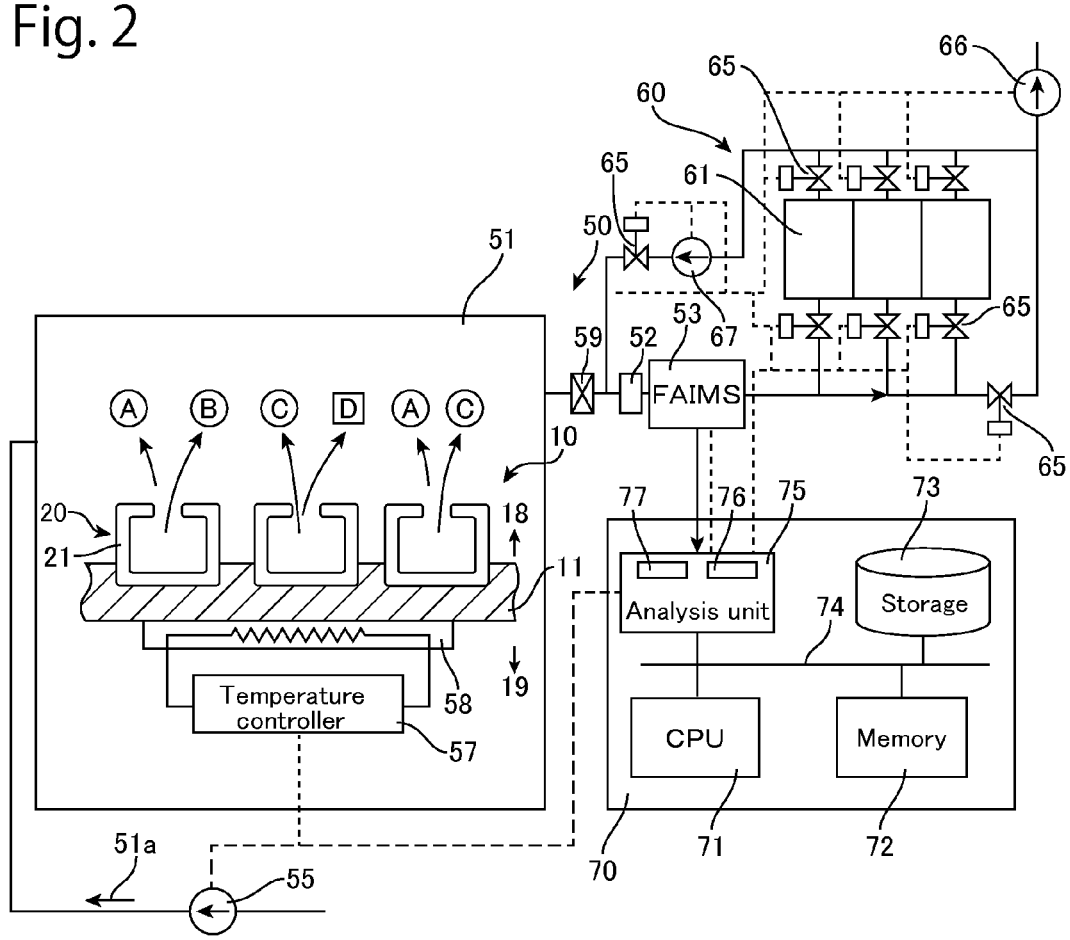
FIG. 2 is a block diagram showing a system that detects chemical substances emitted from a sampler.

FIG. 2 shows an overview of an analyzing system that analyzes the chemical substances sampled by the sampler 10. This analyzing system 50 includes a chamber 51 into which the chemical substances sampled from the sampler 10 are emitted, a sensor 53 that detects the chemical substances, a receiver system 60 for storing the chemical substances emitted from the sampler 10 for reanalysis, and an analysis control apparatus, typically a personal computer (PC) 70.

A typical sensor 53 is an ion mobility sensor (ion mobility spectrometer, ion mobility spectrometry) which ionizes substances (molecules) in air and outputs spectra (ion currents or ion intensities) based on differences in mobility between the ionized molecules. The analyzing system 50 includes an ion mobility sensor 53 called a FAIMS (Field Asymmetric waveform Ion Mobility Spectrometer) or a DMS (Differential ion Mobility Spectrometer). This type of spectrometer (or "sensor", hereinafter FAIMS) 53 inputs ionized molecular flows into an asymmetric electric field that changes from high voltage to low voltage and outputs the result of filtering such flows based on field mobility of the ions. The "micro DMx" made by SIONEX and the FAIMS device made by OWLSTONE can be given as examples of compact FAIMS that are commercially available.

The FAIMS 53 detects chemical substances that have been ionized by an ionizing unit 52 disposed upstream. One example of the ionizing unit 52 is an indirect ionizing unit that uses a nickel isotope (Ni63). The ionizing unit may be an ionizing unit using corona discharge or may be a direct ionizing unit that uses UV.

The chamber 51 for emitting the sampled chemical substances of biological origin from the sampler 10 is a sealed vessel of a construction that enables the sampler 10 to be taken in and out thereof. A heater 58 that heats a non-sampling side (rear surface) 19 on the opposite side to the sampling side (surface) 18 of the sampler 10 and a temperature controller 57 that controls the emission temperature are disposed inside the chamber 51. By controlling the output of the heater 58 that heats the sampler 10, the controller 57 controls the temperature of the sampler 10 (and may be provided with a temperature sensor) and controls the releasing of chemical substances (chemical components, gas molecules) of biological origin temporarily held in the sampler 10. For example, if the temperature is low, substances with a small molecular weight or a small molecular size are outputted from the sampler 10 first, and by raising the temperature, substances with a large molecular weight or a large molecular size are outputted in order from the sampler 10. To enable precise temperature-based control to be carried out, the heater 58 can use a configuration equipped with a plurality of heating elements, such as a line thermal head.

The analyzing system 50 further includes a carrier gas supply pump (blower or fan) 55 that introduces carrier gas (typically dry air) 51*a* into the chamber 51 to convey the chemical substances (for example, A to D) of biological origin to the FAIMS sensor 53 and a filter (particle filter) 59 disposed between the chamber 51 and the FAIMS sensor 53.

The receiver system 60 includes a plurality of receivers 61 that store the exhaust of the FAIMS sensor 53, a valve group 65 that switches lines such as by selecting one or several ones of the plurality of receivers 61 that store the exhaust, a discharge pump (fan or blower) 66, and a recirculation pump (fan or blower) 67. The respective receivers 61 are placed under negative pressure by a vacuum pump or the discharge pump 66 or the like before the start of analysis. The type of chemical substance (A to D) emitted from the sampler 10 heated inside the chamber 51 changes according to the temperature to which the sampler 10 has been heated. The state is confirmed (preanalyzed) according to the output of the FAIMS sensor 53 and by switching the valves 65, the chemical substances emitted to the respective receivers 61 are accumulated so as to be divided into appropriate groups.

Control of the analyzing system 50 and analysis of data obtained by the FAIMS sensor 53 are carried out by the PC 70. The PC 70 includes typical hardware resources that construct a computer, such as a CPU 71, a memory 72, storage 73 such as a hard disk drive, and a bus 74 that connects such components. In addition, the PC 70 includes an analysis unit 75 that controls the analyzing system 50 and analyzes data. The analysis unit 75 may be provided as a semiconductor device such as an ASIC or an LSI, or may be provided as a program (program product) executed by the CPU 71. The analysis unit 75 includes a system controller 76 that controls the FAIMS sensor 53 of the analyzing system 50, the pumps 55, 66, 67, the valves 65, the temperature controller 57, and the like, and an analyzer 77 that analyzes the data of the FAIMS sensor 53. The analysis unit 75 may include a function that acquires environmental conditions such as the temperature, humidity, and pressure of the FAIMS sensor 53 via appropriate sensors and corrects the data obtained from the FAIMS sensor 53.

Figure 3:
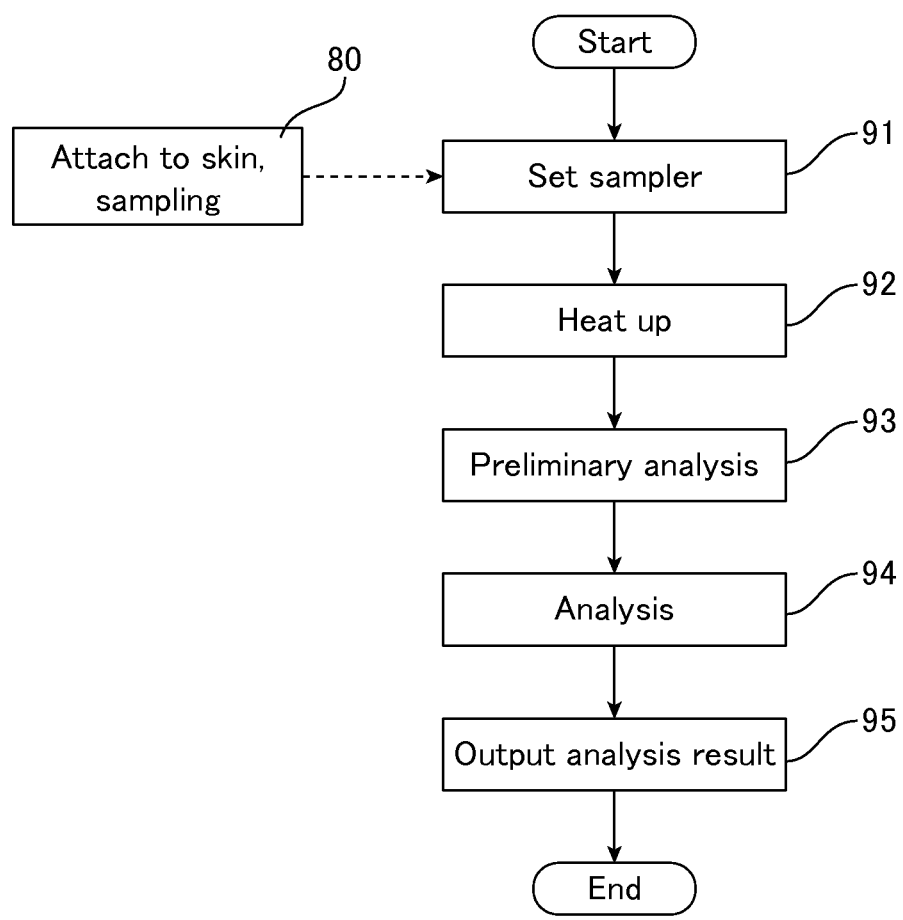
FIG. 3 is a flowchart showing an overview of an analysis method.

FIG. 3 shows the process that analyzes the chemical substances obtained from the sampler 10 in the analyzing system 50. First, in step 80, the sampler 10 is attached to the human body or the body of an animal with the sampling side 18 facing the skin, and chemical substances emitted from the body are extracted or absorbed by the adsorption layer 20 of the sampler 10. In step 91, the sampler 10 separated from the skin is set in the chamber 51 of the analyzing system 50 and in step 92, the non-sampling side 19 of the sampler 10 is heated by the heater 58. In step 93, the chemical substances (A to D) of biological origin emitted from the sampler 10 and preliminarily analyzed by the FAIMS sensor 53 that is an ion mobility sensor. In such preliminary analysis, the analysis unit 75 confirms from the output of the FAIMS sensor 53 that there is a chemical substance emitted due to the heated temperature of the sampler 10, and then during the analysis, divides the chemical substances of biological origin between the plurality of receivers 61 according to the emission temperature so that overlapping of the peaks in the output (spectra) of the FAIMS sensor 53 is comparatively reduced, and temporarily stores the chemical substances in the receivers 61.

When a chemical substance of biological origin has been emitted from the sampler 10, in step 94, by switching between the receivers 61, a chemical substance (including a carrier gas) temporarily stored in the receiver 61 is recirculated to the FAIMS sensor 53 and the chemical substance of biological origin is analyzed in more detail. By using a chemical substance library stored in the storage 73 and/or another database or library accessible via a computer network such as the Internet, the analysis unit 75 utilizes a method such as various fitting methods, simulated annealing, mean field annealing, a genetic algorithm, or a neural network or the like to analyze the chemical substances of biological origin sampled by the sampler 10. In addition, the result of analysis in step 95 is outputted using a display function of the PC 70. An output from the PC 70 via a computer network may also be transmitted to another computer.

Figure 4:
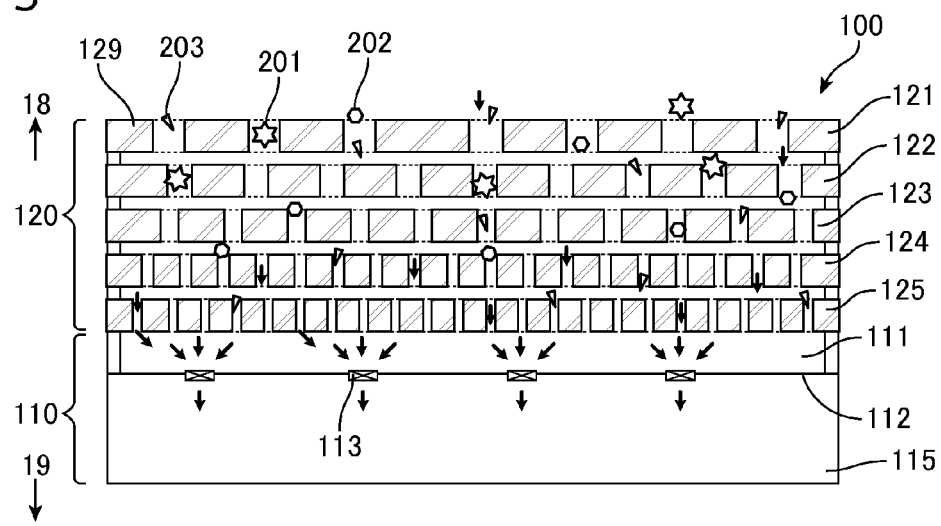
FIG. 4 is a diagram showing sampling by another sampler.

FIG. 4 shows the overall construction of a difference sampling apparatus. This sampling apparatus (sampler) 100 includes an adsorption layer 120 including a plurality of porous layers 121 to 125 that are laminated on the sampling side 18 of the base 110. The plurality of porous layers 121 to 125 include multiple holes of different central pore diameters (central pore diameters, average pore diameters) and such porous layers (porous films) 121 to 125 are laminated in descending order of central pore diameter from the sampling side 18 to the non-sampling side (the base side) 19. As one example, the central pore diameter of the porous layer 121 at the top is 30 nm, the central pore diameter of the second porous layer 124 is 10 nm, the central pore diameter of the third porous layer 123 is 2.0 nm, the central pore diameter of the fourth porous layer 124 is 0.6 nm, and the central pore diameter of the fifth (lowest) porous layer 125 is 0.4 nm. Note that such holes diameters are only illustrated by an example.

In the adsorption layer 120 of the sampler 100, molecules, such as high molecular proteins, with a molecular weight of several thousand kDa are adsorbed by the top layer 121, molecules, such as peptides and comparatively low molecular proteins, with a molecular weight of several tens to several hundred kDa are adsorbed by the second layer 122, and comparatively long chain hydrocarbon compounds and aromatic compounds that are the main cause of body odor and have a molecular weight of several kDa or below are adsorbed by the third layer 123 and the fourth layer 124. Also, although nitrogen and oxygen that are the main constituents of air are adsorbed by the bottom layer (fifth layer) 125, most nitrogen and oxygen passes through the fifth layer 125. Accordingly, in the sampler 100, the intended molecules that are to be sampled are selectively adsorbed by the third layer 123 and the fourth layer 124.

Although the adsorption layer 120 has a five-layer construction, a construction with four or fewer layers or six or more layers may be used. However, to have the intended molecules to be sampled selectively adsorbed and concentrated in an appropriate porous layer, it is preferable to dispose a porous layer with a pore diameter that passes the intended molecules and a porous layer with a pore diameter that does not pass the intended molecules before and after (above and below) such layer. Accordingly, the adsorption layer 120 should preferably be constructed of at least three porous layers with different central pore diameters, with such porous layers being laminated in descending order of the size of central pore diameters from the sampling side 18.

The materials of the porous layers 121 to 125 may be the same or may be different. Examples of the porous layers (films) 121 to 125 are porous glass and zeolite (a molecular sieve or molecular sieves). Zeolite is capable providing a porous layer that includes many pores with comparatively high precision of around 0.1 to several nm. Porous glass can provide a porous layer with many pores with comparatively high precision of around 1 to several hundred nm. The porous layer may be a polymer sheet of a suitable material with a sufficient permeability, for example, a Teflon (registered trademark) sheet.

The thicknesses of the porous layers 121 to 125 should preferably be around 1 μm to 5 mm, with around 1 μm to 1 mm more preferable and around 5 to 500 μm even more preferable. There are no particular limitations on the thicknesses of the respective porous layers, but if the thickness is too low, it is difficult to achieve an adsorption area and if the thickness is too great, the manufacturing cost of producing the multiple pores is too high. Also, if the thickness is too great, the rigidity of the adsorption layer 120 becomes too high, reducing the fit when attached on the skin.

The base (base layer) 110 that supports the adsorption layer 120 includes, from the sampling side 18, a flow control layer 112 and a suction layer 115. The flow control layer 112 is fundamentally an impermeable layer, for example, a thin metal layer, that is disposed on the adsorbent layer 120 with a buffer (gap) 111 that is large enough to allow air to flow. Fine openings 113 are intermittently provided in the flow control layer 112. Such openings 113 are formed by MEMS or the like, for example, and are capable of precisely controlling the airflow that passes through. The openings 113 should preferably be sized so that molecules of the main constituents of air, such as nitrogen and oxygen, pass through without piling up, with a diameter of at least around 0.4 nm being desirable, for example. On the other hand, since the openings 113 are not intended as traps, so long as it is possible to control the amount of flow, there is no particular upper limit on the size. However, with consideration to controlling the flow, openings 113 in a range of around 1 to 10 nm are desirable.

The suction layer 115 is a layer (buffer, region, space) that produces a force that sucks at least one of oxygen and nitrogen through the adsorption layer 120 with a flow amount controlled by the flow control layer 112. In the sampler 100, the suction layer 115 is a low pressure chamber set in advance to negative pressure and air including oxygen and nitrogen is sucked in via the adsorption layer 120 with a flow rate controlled by the difference in air pressure (pressure difference).

Although the chemical substances that are constituents of body odor are adsorbed by the surface (sampling-side surface) of the sampler 100, it is difficult for such chemical substances to penetrate inside the adsorption layer 120 due to voluntary movement such as Brownian motion. In the sampler 100, the suction layer 115 is provided and air is forcibly drawn inside the adsorption layer 120 with a controlled flow rate so that the chemical substances are guided inside the adsorption layer 120 together with the drawn-in air. As described earlier, the adsorption layer 120 has a multilayer construction composed of porous layers and the adsorption surface area inside the adsorption layer 120 is extremely large compared to the surface area of the sampling side 18 surface 129 of the adsorption layer 120. Accordingly, by guiding the chemical substances of biological origin inside the adsorption layer 120, it is possible to adsorb a large amount of chemical substances and to concentrate the chemical substances of biological origin in the specified layers 121 to 125 of the adsorption layer 120.

FIG. 4 schematically shows how the chemical substances 201 to 203 of biological origin are sampled by the sampler 100. The suction layer 115 is placed in advance under negative pressure and the sampling side 18 surface 129 of the adsorption layer 120 is covered with an impermeable sheet, for example, a metal sheet (not shown). Accordingly, first after the metal sheet has been peeled off, by using the same method as that described in FIG. 1, the sampler 100 is attached to the human body or the like with the sampling side 18 facing the skin. Since the adsorption layer 120 includes the porous layers 121 to 125 that have different central pore diameters, a chemical substance 201, such as a protein, with a comparatively large size (diameter or length) will be adsorbed by an upper layer, for example, the top layer 121 or the second layer 122. A chemical substance 202 of an intermediate size, such as an aromatic compound, is adsorbed by the third layer 123 or the fourth layer 124. Chemical substances of a small size such as oxygen, nitrogen, or carbon dioxide are adsorbed by the fifth layer 125 or pass the fifth layer 125 and are sucked into the suction layer 115.

Body odor changes over time, and the chemical substances to be drawn in, such as a chemical substance that is a factor element for determining a disease, will not necessarily be emitted constantly. Accordingly, the flow control layer 112 adjusts the flows that pass through the openings 113 so that the suction force produced by the suction layer 115 can be maintained for around several minutes to several hours. If the suction time is insufficient, it is also possible to attach an external vacuum tank or to attach a vacuum pump to the suction layer 115.

Also, in the sampler 100, the sampling time is controlled by the suction layer 115 and the flow control layer 112. That is, the sampling time is the time until the suction force produced by the suction layer 115 ends, which makes it possible to have automatic control that keeps the sampling time of the sampler 100 constant. For this reason, the person, such as a patient, to which the sampler 100 is attached does not need to manage the sampling time and chemical substances from an organism such as a human body can be precisely extracted.

Figure 5:
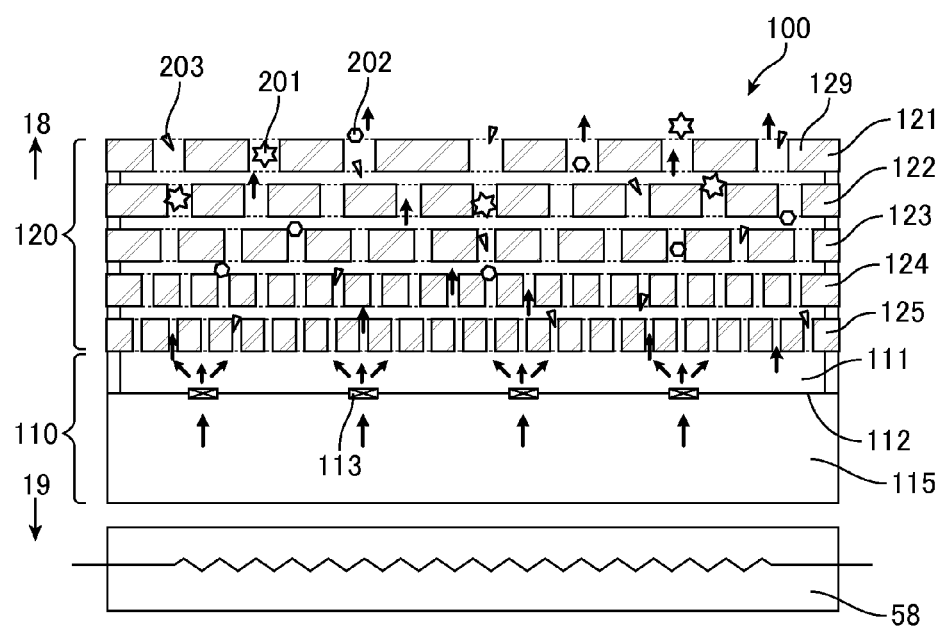
FIG. 5 is a diagram showing how chemical substances are emitted from a sampler.

FIG. 5 shows a state where the chemical substances 201 to 203 of biological origin sampled by the sampler 100 are being emitted. In this state, the sampler 100 is set in the chamber 51 of the analyzing system shown in FIG. 2. When sampling ends, the suction layer 115 is full of air. Due to the non-sampling side (rear surface) 19 of the sampler 100 being heated using the heater 58, the air inside the suction layer 115 expands. Air from the suction layer 115 passes through the flow control layer 112 and flows out to the adsorption layer 120, and the chemical substances 201 to 203 that were adsorbed by the adsorption layer 120 are pushed out of the sampler 100.

Figure 6:
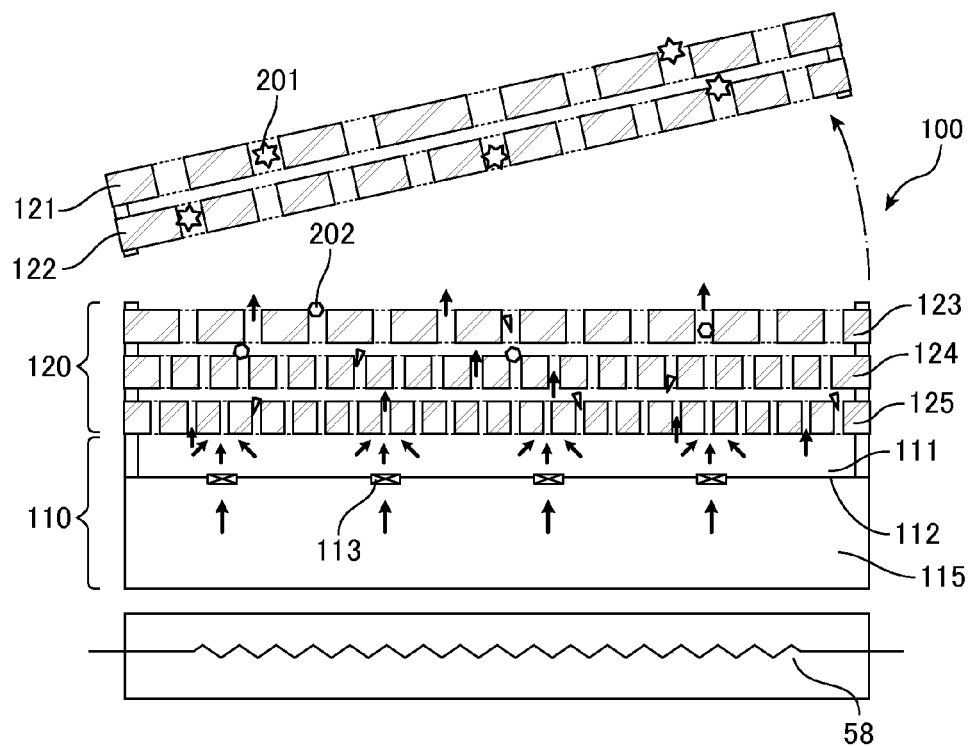
FIG. 6 is a diagram showing how chemical substances are emitted from a sampler according to a different method.

FIG. 6 shows a different method of emitting chemical substances sampled by the sampler 100. In this example, before setting in the chamber 51, the top layer 121 and the second layer 122 of the adsorption layer 120 are removed. Accordingly, even if the sampler 100 is heated inside the chamber 51, the chemical substance 201 that has a comparatively large molecular weight and was caught by the top layer 121 and the second layer 122 will not be emitted and the chemical substance 202 of an intermediate molecular weight (an intermediate size) to be sampled by the sampler 100 will be emitted. Accordingly, in the analyzing system 50, it is possible to mainly analyze chemical substances that are a cause of body odor, such as aromatic compounds, to be sampled by the sampler 100. This means that it is possible to shorten the analysis time and to improve the analysis precision.

Figure 7:
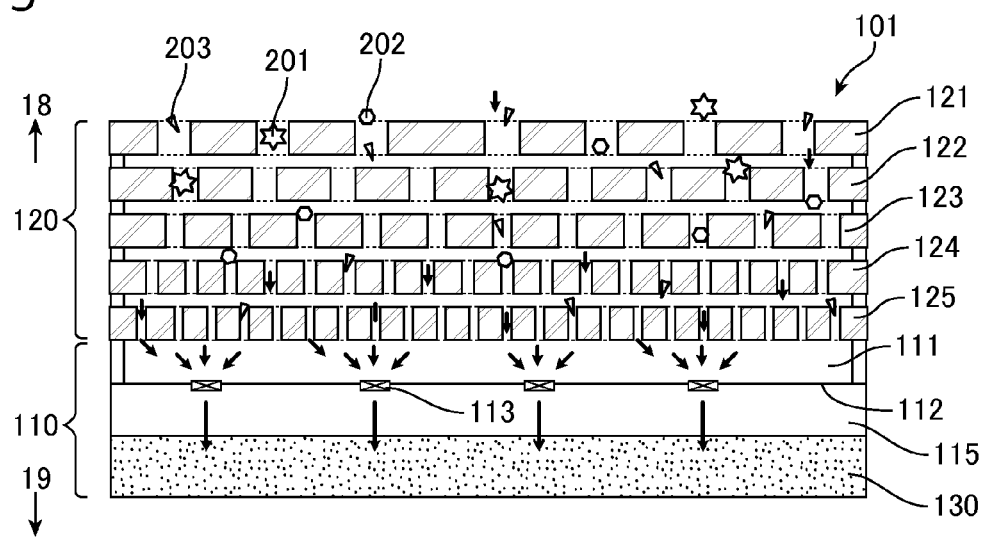
FIG. 7 is a diagram showing sampling by yet another sampler.

FIG. 7 shows an example of yet another sampling apparatus. The fundamental construction of the sampling apparatus (sampler) 100 is the same as the sampler 100 described earlier and includes the adsorption layer 120 including multiple porous layers 121 to 125 and a base (support layer) 110. The base 110 includes the flow control layer 112 and the suction layer 115 and the suction layer 115 includes a molecular sieve (zeolite) layer 130 for suction purposes designed so as to adsorb oxygen and/or nitrogen. For example, LiLSX-type (Li-LowSilica-X-type) zeolite with a hole diameter of 0.3 to 0.4 nm is well known as a molecular sieve for adsorbing nitrogen. Since the chemical substances to be sampled are adsorbed by the upper adsorption layer 120, a molecular sieve layer 130 for suction purposes hardly requires any selectivity for oxygen and/or nitrogen, and it is possible to use a layer with a high adsorption force for gases included in air. Accordingly, the layer is not limited to zeolite (a molecular sieve) and may be a layer that uses another adsorptive material, such as activated carbon.

Also, in place of or together with a layer 130 of an adsorbent for suction purposes, the suction layer 115 may be a reactive layer that reacts chemically with oxygen and/or nitrogen and consumes oxygen and/or nitrogen. An oxidizing reactive layer that has an easily oxidized metal, such as iron, as a main constituent can be given as an example of a layer that consumes oxygen. A layer that forms nitride can be given as an example of a layer that consumes nitrogen, and as one example, a layer that autonomously carries out an ammonia manufacturing process with fullerene as a catalyst is known.

Figure 8:
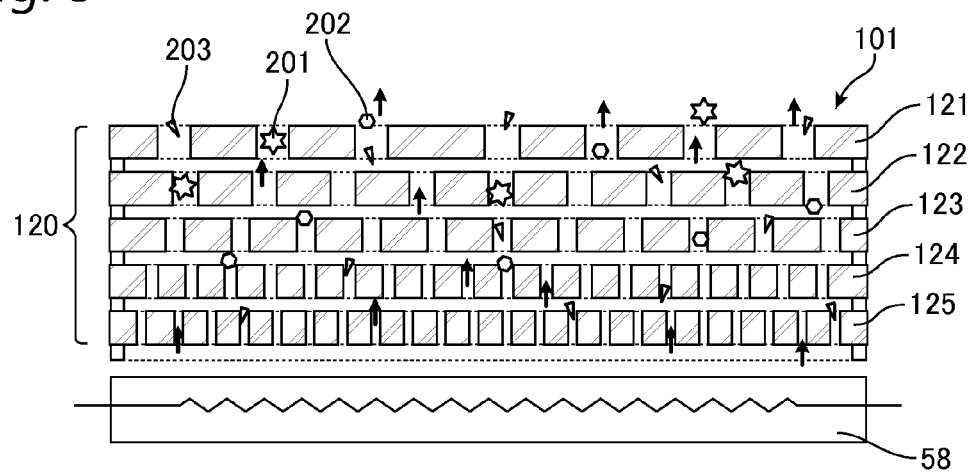
FIG. 8 shows how chemical substances are emitted from a sampler.

FIG. 8 shows one example of a method of emitting chemical substances sampled by the sampler 101. In this example, before setting in the chamber 51, the base 110 is removed from the adsorption layer 120. Accordingly, even if the sampler 101 is heated inside the chamber 51, the constituents sucked onto the base 110 will not be emitted. Accordingly, with the analyzing system 50, it is possible to mainly analyze chemical substances, such as aromatic compounds, that are the cause of body odor and are to be sampled by the sampler 101. This means that the analysis time can be reduced and the analysis precision can be raised.

Figure 9:
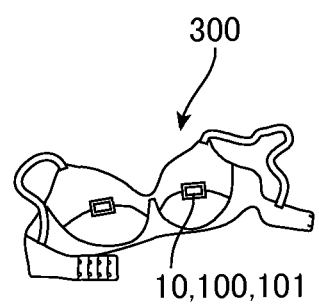
FIG. 9 is a diagram showing how samplers are attached to underwear.

FIG. 9 shows how the samplers 10, 100, or 101 (hereinafter simply "10") are attached to ladies' underwear. By fixing the samplers 10 to underwear, for example, the brassiere 300, so that the sampling side 18 of the samplers 10 face the nipples or the skin in the vicinity, it is possible to sample chemical substances of biological origin that are emitted in the vicinity of the nipples. It is known that at the onset of breast cancer, chemical substances (markers) with a smell are emitted. Accordingly, by sampling the marker substances using the sampler 10 and carrying out analysis with the analyzing system 50, it is possible to easily and precisely determine the presence or absence of breast cancer. Since it is possible to precisely determine the presence or absence of breast cancer simply by wearing the brassiere 300 that includes the samplers 10 for a short time, for example, from several minutes to several hours, there is a further effect in that the load upon the human body (excessive physical burden) can be reduced.

When directly measuring chemical substances (chemical constituents, molecules, and compositions) included in the exhaled breath or skin respiration of the throat or another affected part of a human or an animal using an analyzing system, there is the problem of having to maintain a constant sample flow and the problem of the difficulty in measuring continuously for a long time, such as twenty-four hours. In particular, in the case of an animal such as a pet, it is difficult to connect the animal to an analyzing system without a struggle. It is also presently difficult to fix an analyzing system itself to the human body or the body of an animal.

In addition, the chemical substances included in the exhaled breath or skin respiration of the throat or another affected part of a human or an animal exist in extremely small amounts, which makes accurate measurement difficult. With a FAIMS sensor or the like, it is possible to specify or analyze chemical substances of extremely fine amounts with extremely high precision of ppb or ppt order or smaller, and by specifying chemical substances called marker substances produced by cancer or another illness, it is possible to establish the initial state of a disease or the progress of a disease. Accordingly, the sampler 10 described above is favorable for sampling extremely small amounts of chemical substances of biological origin.

For example, if analysis of chemical substances is carried out by GC-MC (gas chromatography and mass spectrometry), the range of detection concentration is several ppm to several ppb. At concentrations below ppb, it is difficult to detect the chemical substances to be sampled without concentrating the substances. When detecting chemical substances with extremely low concentrations, it is possible to use a method called SPME (Solid Phase Micro Extraction). The intended chemical substances are selectively extracted from a liquid sample, a solid sample, or a gas sample, and high sensitivity detection is realized by GC-MS. However, the sampled amount needs to be at least 100 µliters, and an extraction time of around 10 to 30 minutes is required. When a plurality of markers substances are to be detected, it is necessary to provide a plurality of SPME. In addition, to guarantee the proper prescribed analysis values, it is necessary to reduce the effect of sampling errors and necessary to perform a certain number of measurements. In particular, when specifying a disease such as cancer from skin respiration, intraluminal breath odor or saliva, there are many issues to be solved such as the problem of errors due to secondary extraction from the subject or the sampling medium and the problem of sampling time. For example, if a patient tries to correctly control the sampling time, the amount of trapped marker substances will change, which can lead to errors. When considering the detection of cancer, GC-MS analysis for diseases, and the determination process, tens of hours are required for determination.

On the other hand, with the present sampling apparatus, a construction that uses porous glass is referred to as PGAS (Porous Glass Auto Sampling), for example and by disposing layers of granular porous glass with pores of different diameters on top of one another in multiple layers, it is possible to trap chemical substances while carrying out control to keep the flow and the time constant. The diameters of the pores in the porous glass can be changed on the various layers in keeping with the target marker substances to be trapped for the cancer or disease to be detected. The control of flow may use a method in which the diameters of openings for controlling the negative pressure of a flow control layer are selected and the time is controlled. By selecting the pressure of negative pressure side and the diameters for flow control, it is possible to accurately control the sampling time in keeping with the test purposes from several tens of seconds to several hours. The method of trapping the chemical substance does not need to use porous glass. However, as the adsorbent, it is necessary to select a material with favorable response and performance, including resistance to reacting with chemical substances, long-term storage stability, selective trapping performance for the marker substances in a short time when measurement analysis has commenced and conversely release performance when heat is applied. For such reasons, porous glass is extremely favorable and has the required properties.

Note that although a sampler attached to the human body or the body of an animal has been described above as an example, the sampler (sampling apparatus) may be placed in contact not only with skin but also exhaled air and sample chemical substances included in exhaled air. The sampler is also not limited to chemical substances of biological origin and it is also possible to sample chemical substances included in a container, a room, or the like. By using such sampling apparatus, it is possible to easily raise the concentration of chemical substances and to sample chemical substances at a different time and different location to the sensor system (analyzing system). Accordingly, the sampling method removes temporal and locational limitations on sample collection, removes the limitations on concentration, and increases the potential of sampling. In addition, the sampling apparatus is not limited to chemical substances and is also capable of capturing bacteria, viruses, and cells. Also, by changing the material of the adsorption layer, the size of the fine pores, and the like, it is possible to achieve a selective performance for the subject to be collected.

The invention claimed is:

1. A sampling apparatus of chip-type to be attached so that a sampling side of the sampling apparatus faces the skin, comprising:
   a porous adsorption layer that faces the sampling side and has a pore diameter in a range of 0.1 to 1000 nm; and
   a suction layer disposed, via a flow control layer that controls passing airflow, on a non-sampling side of the adsorption layer and sucks at least one of oxygen and nitrogen through the adsorption layer, the non-sampling side being an opposite side to the sampling side of the adsorption layer.

2. The sampling apparatus according to claim 1,
wherein the porous adsorption layer includes at least three porous layers with different central pore diameters laminated from the sampling side in descending order of central pore diameters.

3. The sampling apparatus according to claim 1,
wherein the suction layer includes a material that adsorbs at least one of oxygen and nitrogen.

4. The sampling apparatus according to claim 1,
wherein the suction layer includes a material that reacts with at least one of oxygen and nitrogen.

5. The sampling apparatus according to any of claim 1,
wherein the adsorption layer includes a porous glass layer.

6. A method comprising:
attaching a sampling apparatus according to claim 1 with the sampling side facing the skin and collecting a chemical substance emitted from an organism in the adsorption layer; and
heating the sampling apparatus that has been separated from the skin and analyzing a chemical substance of biological origin emitted from the sampling apparatus using an ion mobility sensor.

* * * * *